United States Patent [19]
Zengel et al.

[11] 3,965,172
[45] June 22, 1976

[54] PRODUCTION OF N,N-DICHLORO-TEREPHTHALAMIDE AND N,N-DICHLORO-ISOPHTHALAMIDE

[75] Inventors: Hans-Georg Zengel, Kleinwallstadt; Manfred Bergfeld, Erlenbach, both of Germany

[73] Assignee: Akzona Incorporated, Asheville, N.C.

[22] Filed: Mar. 13, 1974

[21] Appl. No.: 450,674

[30] Foreign Application Priority Data
Mar. 19, 1973 Germany............................ 2313548

[52] U.S. Cl............................. 260/543 A; 424/315
[51] Int. Cl.$^2$............... C07C 119/18; C07C 135/00
[58] Field of Search.............................. 260/543 A

[56] References Cited
UNITED STATES PATENTS

| | | | |
|---|---|---|---|
| 3,105,848 | 10/1963 | Linder et al. | 260/471 C |
| 3,657,324 | 4/1972 | Sheppard et al. | 260/543 A |

FOREIGN PATENTS OR APPLICATIONS

| | | |
|---|---|---|
| 749,976 | 12/1944 | Germany |
| 616,381 | 7/1935 | Germany |
| 878,491 | 6/1953 | Germany |
| 909,455 | 4/1954 | Germany |

OTHER PUBLICATIONS

Datta et al., J. Am. Chem. Soc. 35 1044 (1913).

*Primary Examiner*—Norman Morgenstern
*Attorney, Agent, or Firm*—Johnston, Neil, Thompson & Shurtleff

[57] ABSTRACT

Preparation of N,N'-dichloro-terephthalamide or N,N'-dichloro-isophthalamide by chlorination of an aqueous suspension of the corresponding terephthalamide or isophthalamide under acid conditions in which the dilution of the reaction mixture is sufficient to maintain the hydrogen chloride being produced as a by-product of the chlorination substantially completely dissolved in the reaction mixture up to the end of the reaction. The compound N,N'-dichloro-terephthalamide has been discovered to be a very stable mild oxidizing agent useful as an antiseptic. Both compounds obtained by the disclosed preparation are valuable intermediate compounds.

9 Claims, No Drawings

PRODUCTION OF N,N-DICHLORO-TEREPHTHALAMIDE AND N,N-DICHLORO-ISOPHTHALAMIDE

It is generally known that one can halogenate lower aliphatic carboxylic acid amides in their molten state or in an aqueous solution to form the corresponding N-haloamides. Saturated and unsaturated higher molecular weight N-chloro-fatty acid amides having more than 16 carbon atoms can also be produced if chlorine is permitted to act upon the corresponding water-insoluble fatty acid amides finely dispersed in water (German Pat. Nos. 749,976 and 878,491).

It is also possible to convert some aromatic carboxylic acid amides into the corresponding N-halogen compounds by chlorination or bromination. According to R. L. Datta and T. Ghosh (Journ. Am. Chem. Soc. Vol. 35 (1913), page 1044), N-chlorobenzamide is obtained in quantitative yields by conducting a stoichiometric amount of chlorine gas into a solution of benzoic acid amide within a few hours. If the chlorine is used in excess, the primary product is N-dischlorobenzamide. According to the process disclosed in German patent specification No. 616,381, aliphatic and also aromatic N-chlorocarboxylic acid amides are to be produced by suspending the carboxylic acid amide in an aprotic liquid, such as carbon tetrachloride or dichlorobenzene, and then conducting chlorine into the suspension which preferably contains a binding agent for hydrochloric acid.

If one attempts to transfer these processes known for the various monoamides to aliphatic alicyclic and araliphatic dicarboxylic haloamides, only very slight yields are obtained at best. According to the process of German patent specification No. 909,455, the yields of some reactions may be improved by carrying out the halogenation in the presence of an agent binding hydrogen halide, e.g. sodium bicarbonate, and by using as the solvent water, acetic acid or another organic acid under addition of alkali or alkaine earth metal salts of these organic acids. However, the carboxylic acid amide may also be mixed dry with the hydrogen halide binding agent, halogen vapor then being conducted over the dry mixture.

In spite of such extensive prior experimentation, no suitable process has been found for the production of aromatic N,N'-dihalocarboxylic acid amides. Only in U.S. Pat. No. 3,105,848 is there disclosed a production of N,N'-dichloro-isophthalamide by chlorination of isophthalamide in nitrobenzene and in the presence of sodium carbonate. In the final steps of this known process, N,N'-dichloro-isophthalamide is obtained in a yield of only 3.5% of theory.

The previously unknown N,N-dichloro-terephthalamide is not produced by this process of U.S. Pat. No. 3,105,848 or by any other known process. Thus, it will be found that the process used for the production of N-halogen monoamides do not lead to the desired product. In attempting to chlorinate terephthalamide in the presence of sodium or potassium hydroxide, we have obtained only small amounts of the desired N,N'-dichloro-terephthalamide. With the use of sodium carbonate or bicarbonate, practically no N-chloro compounds have been obtained, but instead only large amounts of terephthalic acid were formed by saponification.

Chlorinating phthalamides in organic solvents likewise fails to bring about the desired result. With the use of carbon tetrachloride or chlorobenzene, the initial terephthalic acid amide reactant was recovered quantitatively. When acetic acid was tried as the solvent, the yield of N,N'-dichloro-terephthalamide amounted to only 2.3% of theory.

One object of the present invention is to provide a process for the preparation of the previously unavailable compound identified herein as N,N'-dichloro-terephthalamide and having the formula:

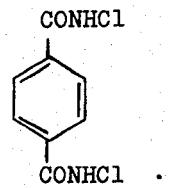

It is also an object of the present invention to employ this same process as a preferred means of producing the known compound identified herein as N,N'-dichloro-isophthalamide and having the formula:

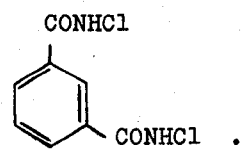

These objects and advantages of the invention will become more apparent upon consideration of the following detailed disclosure.

It has been found, in accordance with the invention, that one can readily produce N,N'-dichloro-terephthalamide or N,N'-dichloro-isophthalamide from the corresponding terephthalamide or isophthalamide, respectively, as the initial phthalamide reactant by reacting chlorine with this initial reactant suspended in water while maintaining the resulting reaction mixture over the course of the reaction as a dilute aqueous solution of a mineral acid, the dilution being such that the hydrogen chloride formed by the chlorination reaction remains substantially completely dissolved in the reaction mixture.

The success of the present reaction was quite unpredictable. On the one hand, the process of chlorination in a non-aqueous medium and using a hydrogen chloride acceptor leads to satisfactory yields when generally applied to aliphatic, alicyclic and araliphatic mono- and di-carboxylic acid amides but completely fails to work in the case of terephthalamide and isophthalamide. On the other hand, the use of an aqueous mineral acid reaction medium which has proved to be successful with terephthalamide and isophthalamide as initial reactants in the present invention does not give satisfactory results either with aliphatic, alicyclic and araliphatic mono- and di-carboxylic acid amides or with aromatic monocarboxylic acids such as benzamide. With such other reactants, the process of the present invention gives only slight yields and/or requires very long reaction times. This remarkable difference in results is even more surprising when one considers the fact that terephthalamide and isophthalamide, in contrast for example to benzamide, are completely insoluble in an aqueous mineral acid medium. Finally, it should be noted that an attempt to prepare the already known N,N'-dibromo-terephthalamide by bromination in a dilute aqueous HCl or HBr solution also meets with total failure, so that the results of the present invention are both unique and extraordinary.

As an aqueous mineral acid medium, it is preferable for the process of the present invention to employ a dilute aqueous solution of hydrochloric acid, sulfuric acid, phosphoric acid or mixtures thereof.

In one embodiment of the invention, the reaction can be advantageously initiated with a mixture consisting essentially of a neutral suspension of the terephthalamide or isophthalamide reactant, whereby the hydrogen chloride formed as a by-product by the chlorination reaction becomes dissolved in the reaction mixture and the reaction thus proceeds in a dilute aqueous hydrochloric acid medium. It is further preferred to proceed from initial dilute hydrochloric acid or dilute sulfuric acid aqueous suspensions of the phthalamide reactant.

The yield and the rate of chlorination in the process of the invention depend strongly on the acid concentration in the reaction mixture. Since the acid concentration of the reaction mixture or aqueous medium increases regularly as the chlorination progresses due to the release of hydrogen chloride, the rate of chlorination is retarded as the reaction comes closer to completion. Thus, if one proceeds from a strongly concentrated acid medium, e.g. from a 50% by weight sulfuric acid or from a 25% by weight hydrochloric acid solution, only slight yields are achieved. In even more concentrated hydrochloric or sulfuric acid initial reaction mixtures, there is practically no reaction.

Moreover, if the acid concentration in the reaction exceeds a certain maximum value during the course of the chlorination, the reaction is rapidly retarded. This maximum value of the acid concentration, which one should not exceed, is specific for each mineral acid and it also depends upon the reaction temperature and reaction pressure. It has been found, in fact, that this maximum value is reached when the hydrogen chloride arising in the course of the chlorination can no longer be completely dissolved in the reaction mixture, i.e. when the saturation concentration of the hydrogen chloride in the reaction mixture is exceeded under the given reaction conditions. These saturation concentrations can be easily determined for various reaction conditions by routine experimentation.

Since the amount of hydrogen chloride being released as a by-product in the reaction may be calculated directly from the amount of the initially introduced phthalamide reactant, it is preferable to select in initial dilution of the reaction mixture which is sufficiently low to avoid exceeding the saturation concentration of hydrogen chloride at the end of the reaction. However, it will be evident that the reaction mixture can also be further diluted during the course of the reaction by adding water or a dilute mineral acid.

The chlorination of both terephthalamide and isophthalamide proceeds exothermically, i.e. with heat being generated by the reaction itself. In general, the reaction is preferably carried out in accordance with the invention at temperatures of about 0°C. to 100°C. The use of higher temperatures is disadvantageous insofar as noticeable amounts of terephthalic acid or isophthalic acids are formed by hydrolysis under these conditions. For economical reasons, the chlorination is preferably carried out at about 0°C. to 60°C., the heat of reaction being easily removed by water cooling or by cooling with other fluid heat transfer media.

The process of the invention can be carried out at normal (atmospheric) pressure or at higher pressures. With increasing chlorine pressures, the required reaction time decreases, but the chlorine pressure range of between about 1 and 20 atm. is preferred for economical reasons. Either a liquid or gaseous chlorine may be used depending upon the chosen conditions of pressure and temperature.

Since the chlorination reaction according to the invention is a process carried out in a heterogeneous phase, good mixing of the suspension is desirably provided. The dilution of the reaction mixture should at least be regulated such that it can be stirred without difficulties or otherwise thoroughly mixed. The preferred dilution or proportion of the initial phthalamide reactant is about 20 to 400 grams of amide per liter of water or aqueous mineral acid.

By following the cited process conditions, the chlorination can be completed after about 2 to 60 minutes. The initial phthalamide is practically quantitatively converted into the corresponding N,N'-dichloro-terephthalamide or N,N'-dichloro-isophthalamide without any intermediate formation of a solution. The suspension present at the end of the chlorination contains as solids substantially only the desired product. This solid product can be separated and recovered in the easiest possible manner, for example by simple filtration or centrifuging. After washing, e.g. with cold water, and then drying, e.g. at approximately 70°C. under vaccum, the product can be obtained in very pure form.

The N,N'-dichloro-terephthalamide produced according to the invention is a colorless, microcrystalline substance, turning light gray and sintering slightly at 250°C. and tending to sublime at 300°C. It is moderately soluble in polar organic solvents, e.g. in dioxane, dimethylacetamide, dimethylformamide and hexamethylphosphoric acid triamide. N,N'-dichloro-terephthalamide can be maintained in a darkened container for a practically unlimited period of time. At room temperature, it is a mild oxidation agent. By reason of its outstanding stability, it can be advantageously used for example in place of the less stable antiseptic agent Chloramin T (Sodium-N-chloro-p-toluenesulfonamide).

N,N'-dichloro-isophthalamide is a known compound and both it and the isomeric N,N'-dichloro-terephthalamide represent valuable intermediate compounds. They may be converted into substituted ureas by reaction with amines, such ureas being used as herbicides and pesticides. Both products of the invention also have the utility described for N,N'-dichloro-isophthalamide in U.S. Pat. No. 3,105,843 (Example 3 and col. 6, lines 38–42). Moreover, both compounds may be converted by treatment with alkali or alkaline earth metal hydroxides into the corresponding meta- and para-phenylene-diamines which have a known utility as described in Kirk-Othmer, 2nd Edition, pages 222–223, (Vol. 15).

The invention is further illustrated by but not limited to the following examples.

EXAMPLE 1

540 grams (3.20 mols) of terephthalamide were suspended in 10 liters of water. Chlorine was conducted into this suspension with intensive mixing at a rate of 4 grams/min. over a period of 2 hours. By slightly cooling, the reaction temperature was maintained at 25°C. The pressure amounted to 1 atmosphere, i.e. the reaction was carried out at normal pressure. The reaction mixture was then filtered, the residue washed with 2 liters of cold water and dried at 70°C. under a vacuum. 755 grams (98.4% of theory) of colorless N,N'-dichloro-terephthalamide was obtained as the product.

EXAMPLE 2

32 grams (0.195 mols) of terephthalamide were suspended in 0.6 liters of a 17% by wt. hydrochloric acid solution in a glass autoclave. 33 grams of chlorine were introduced at 6 atm. while stirring and cooling at 25°C. After 8 minutes, a constant pressure was reached in the autoclave, thereby indicating the completion of the reaction. The reaction mixture was then worked up as in Example 1. The yield of pure N,N'-dichloro-terephthalamide amounted to 44.2 grams (97.2% of theory).

EXAMPLE 3

1,200 grams (7.317 mols) of terephthalamide were suspended in 7 liters of a 17% by weight aqueous hydrochloric acid solution. Into this suspension, there was conducted 1,100 grams chlorine at 25°C. over a period of 30 minutes in such a manner that the pressure was maintained constant at about 6 atm. Thereafter, the reaction mixture was worked up as in Example 1. The yield amounted to 1,690 grams (99.1% of theory) of N,N'-dichloro-terephthalamide.

EXAMPLE 4

Into a suspension of 400 grams (2.439 mols) of terephthalamide in 1 liter of 17% by weight hydrochloric acid under normal pressure, at 55°C. and within about 140 minutes, there was introduced 360 grams of chlorine gas. The working up of the reaction mixture then proceeded as in Example 1. The yield of N,N'-dichloro-terephthalamide amounted to 522 grams (92% of theory)

EXAMPLE 5

Into a suspension of 5 grams (0.0305 mols) of terephthalamide in 200 ml. of a 10% aqueous sulfuric acid, under stirring at normal pressure and a temperature of 25°C. over a 2 hour period, there was introduced chlorine gas at a rate of about 0.1 grams minute. The resulting N,N'-dichloro-terephthalamide was filtered off, washed with water and dried. The yield amounted to 6.94 grams (97.7% of theory).

EXAMPLE 6

64 grams (0.39 mols) of terephthalamide were suspended in 500 ml. of a 15% aqueous hydrochloric acid. Under stirring at room temperature and normal pressure, 90 grams of gaseous chlorine were conducted into the suspension within a period of 3 hours. Thereafter the reaction mixture was filtered, the residue washed with cold water and dried. There was obtained 90 grams (99.0% of theory) of N,N'-dichloroisophthalamide with a melting point of 73.5°–75°C.

EXAMPLE 7

16.4 grams (0.10 mols) of terephthalamide were suspended in 500 ml. of a 17% by weight hydrochloric acid solution and heated in an enamel autoclave at 34°C. Then, by means of a dosing bulb and under intensive mixing, 22.8 grams (0.32 mols) of liquid chlorine was introduced into the autoclave. With water cooling, the reaction temperature was maintained at about 35°C. The reaction pressure amounted to 10 atm. After 5 minutes, the reaction from the autoclave, filtered and the residue washed with 200 ml. of water. The residue was then dried under vacuum at 70°C. There resulted 22.6 grams (97% of theory) of N,N'-dichloro-terephthalamide.

EXAMPLE 8

16.4 grams (0.10 mols) of terephthalamide were suspended in 500 ml. of 17% by weight aqueous hydrochloric acid and rapidly heated up to 45°C. in an enamel autoclave. Then, by means of a dosage bulb, under mixing and water cooling, 23 grams (0.325 mols) of liquid chlorine were conducted into the autoclave whereby the temperature rose to 55°C. and the pressure to 20 atm. within about 30 seconds. After 3 minutes, the reaction mixture was discharged from the autoclave and filtered. The residue was washed with 200 ml. of water and dried under vacuum at 70°C. The yield of N,N'-dichloro-terephthalamide amounted to 94% of theory.

COMPARATIVE EXAMPLES

The following comparative experiments in Examples 9 to 13 were carried out to provide that conventional processes known to be suitable for the production of N-chloro- or N,N'-dichloro-carboxylic acid amides from aliphatic, alicyclic, araliphatic or even aromatic carboxylic acid amides, do not work when attempting to produce either N,N'-dichloro-terephthalamide or N,N'-dichloro-isophthalamide.

EXAMPLE 9

8.2 grams (50 millimols) of terephthalamide were suspended in a solution of 8.7 grams (103 millimols) sodium bicarbonate in 450 ml. water. Under strong mixing, 7.1 grams (100 millimols) chlorine were introduced at 5°C. within a period of 30 minutes. Thereby arose a vigorous evolution of carbon dioxide. After completion of the reaction (pH-value = 7.5), the mixture was filtered and the residue then suspended in a dilute caustic soda solution at 2°–5°C., cooled to a −5°C. and finally filtered by use of a glass frit. As residue, there remained 6.23 grams (38 millimols) of unreacted terephthalamide, corresponding to a reaction of 24% of theory. The filtrate was then dropped at 0°C., into acetic acid whereby terephthalic deposited as voluminous, white precipitate. It was washed with ice water and dried over $P_2O_5$ to yield 1.85 grams (11 millimols) of the acid. N,N'-dichloro-terephthalamide was not obtained in this example.

EXAMPLE 10

8.2 grams (50 millimols) terephthalamide were suspended in 400 ml. water and at 5°C. quickly mixed with a sodium hypochlorite solution prepared from 26.5 grams (250 millimols) sodium carbonate in 500 ml. water and 7.1 grams (100 millimols) chorine. The reaction mixture was strongly mixed for a period of 4 hours at 10°C. The non-reacted terephthalamide was then filtered off to recover 5.69 grams (34.7 millimols) filtered off to recover 5.69 grams (34.7 millimols). The reacted terephthalamide thus amounted to 30.6%. The terephthalic acid resulting from saponification was then separated from the filtrate by precipitation in acetic acid as described in Example 9 to yield 2.62 grams (15.8 millimols), corresponding to 31.7% of theory. Also in this method of working, no N,N'-dichloro-terephthalamide could be obtained.

EXAMPLE 11

8.2 grams (50 millimols) terephthalamide were suspended in 500 ml. water under nitrogen and slowly mixed at 5°C. with a solution freshly prepared from 20.0 grams (500 millimols) NaOH, 400 ml. water and 7.1 grams (100 millimols) $Cl_2$. The reaction mixture was then strongly mixed for 4 hours at 10°C., then cooled to a −5°C. and filtered over a glass frit. The white residue, which was washed twice with cold water and dried, consisted of unreacted terephthalamide in an amount of 4.8 grams (29.4 millimols). The conversion therefore amounted to 41.4% of theory.

The filtrate was cautiously dripped into a solution of 50 ml. glacial acetic acid and 100 ml. water at 0°–7°C. within about 15 minutes. There was deposited a voluminous, curdy precipitate which was separated by means of a glass frit, washed well with ice water and then dried over phosphorous pentoxide at room temperture. This crude product, 4.90 grams of a bright yellow powder, was digested in 50 ml. of chloroform. After filtration, there was obtained as a residue 1.61 grams (10.9 millimols) of N,N'-dichloro-terephthalamide. This corresponds to a yield of only 16.1% of theory at a selectivity of only 38%.

From the chloroform phase, the previously unknown terephthalic acid-bis-dichloramide crystallized in the form of yellow needles. Yield = 3.29 grams (25.3% of theory at a 61.2% selectivity). This substance, by comparison to N,N'-dichloro-terephthalamide, has a strong oxidation effect and is characterized by good solubility in organic solvents, especially in chlorinated hydrocarbons.

EXAMPLE 12

8.2 grams (50 millimols) of terephthalamide were suspended in 50 ml. of water and added at 0°–5°C. over a period of 30 minutes while mixing under a nitrogen atmosphere to a solution of 32.7 grams (500 millimols) of 86% potassium hydroxide, 7.10 grams (100 millimols) of chlorine and 400 ml. of water. The reaction mixture was mixed for 5 hours at the specified temperature. The reaction mixture became thinly fluid or watery with a yellow-brown coloration. The suspension was then filtered and worked up in the manner as described in Example 11. 5.988 grams of terephthalamide were recovered. The conversion therefore amounted to 2.21 grams (13.5 millimols), corresponding to 27% of theory. From the filtrate, in a manner analogous to Example 11, there were isolated 3.3 grams (11 millimols, 22% yield) of terephthalic acid bis-dichloramide and 5% of theory of N,N'-dichloro-terephthalamide.

EXAMPLE 13

41 grams (0.25 mols) terephthalamide were suspended with 10.3 grams (0.125 mols) of sieved zinc oxide in 300 ml. of water at 2°C. Chlorine was introduced into the suspension over 1 and one-half hours at 0°–5°C. in an amount of 71 grams (1.0 mol), and the mixture stirred for 6 hours at 5°C. After filtration, the formed N,N'-dichloro-terephthalamide was separated from the unreacted terephthalamide with a 2N caustic soda solution (NaOH) at 5°C. This was then precipitated in acetic acid and worked up as in Example 11. There was recovered 35.2 grams (0.214 mols) of terephthalamide. The conversion thus amounted to only 11.7% of theory. The yield of N,N'-dichloro-terephthalamide amounted to 0.757 grams (0.0325 mols) = 7.7% of theory. About 4% of the terephthalamide was saponified to terephthalic acid.

The next three comparative Examples 14–16 show that the chlorination of terephthalamide in various organic solvents provides no yield at all or only very slight yields of N,N'-dichloro-terephthalamide.

EXAMPLE 14

Into a suspension of 41 grams (0.25 mols) of terephthalamide in 160 ml. of glacial acetic acid, there was introduced 213.0 grams (3.0 mols) of chlorine with strong mixing over approximately 16 hours at 18°–20°C. Then, the residue of terephthalamide and N,N'-dichloro-terephthalamide were filtered off and washed with water. The separation of these two compounds took place with dilute caustic soda solution and then precipitation with acetic acid. 39.9 grams of unreacted terephthalamide were recovered. The yield of N,N'-dichloro-terephthalamide amounted to 1.35 grams (58 millimols), corresponding to 2.3% of theory.

EXAMPLE 15

Into a suspension of 41 grams (0.25 mols) of terephthalamide in 500 ml. of carbon tetrachloride, there was introduced 265 grams (3.74 mols) of chlorine with vigorous mixing within about 12 hours at 10°C. The reaction mixture was then worked up as described in Example 13. The terephthalamide was quantitatively recovered; the formation of N,N'-dichloro-terephthalamide could not be detected.

EXAMPLE 16

121 grams of chlorine were introduced with strong mixing over a period of 3.5 hours into a suspension of 41 grams (0.25 mols) of terephthalamide in 250 ml. of chlorobenzene maintained at boiling temperature (132°C.). Thereby sublimed approximately 5.4 grams of colorless crystals. They proved to be hexachlorobenzene which had resulted from chlorination of the solvent. The initial terephthalamide was quantitatively recovered.

From the final two comparative examples, it will be noted that the known N,N'-dibromo-terephthalamide cannot be obtained by using the process of the present invention.

EXAMPLE 17

16.4 grams (100 millimols) terephthalamide were suspended in 180 ml. of a 10% aqueous hydrobromic acid solution, and 32 grams (200 millimols) of bromine were added dropwise at 20°C. The reaction mixture was next stirred for 24 hours and then filtered. The residue was washed and dried. There was obtained 16.2 grams or practically all of the initial terephthalamide.

EXAMPLE 18

16.4 grams (100 millimols) terephthalamide were suspended in 180 ml. of 10% aqueous hydrochloric acid and 32 grams bromine added dropwise at 20°C. After 5 hours, the reaction mixture was worked up as described in Example 16. The terephthalamide was quantitatively recovered.

The invention is hereby claimed as follows:
1. A process for the production of N,N'-dichloro-terephthalamide or N,N'-dichloro-isophthalamide from the corresponding terephthalamide or isophthalamide as the initial phthalamide reactant, which process comprises:

reacting chlorine at a temperature of about 0°C. to 100°C. with said phthalamide reactant suspended in a liquid reaction mixture which, over the course of the reaction, consists essentially of a dilute aqueous solution of a mineral acid, the dilution being such that all of the hydrogen chloride formed by the chlorination reaction remains substantially completely dissolved in the reaction mixture.

2. A process as claimed in claim 1 wherein the reaction is carried out at a pressure of about 1 to 20 atmospheres.

3. A process as claimed in claim 2 wherein the reaction temperature is about 0°C. to 60°C.

4. A process as claimed in claim 1 wherein the reaction is initiated in a neutral aqueous suspension of said phthalamide.

5. A process as claimed in claim 1 wherein the reaction is initiated in a dilute hydrochloric acid suspension of said phthalamide.

6. A process as claimed in claim 1 wherein the reaction is initiated in a dilute sulfuric acid suspension of said phthalamide.

7. A process as claimed in claim 1 wherein the amount of said initial phthalamide reactant is about 20 to 400 grams per liter of the aqueous reaction mixture.

8. A process as claimed in claim 7 carried out as a batch process over a period of about 2 to 60 minutes.

9. A process as claimed in claim 8 in which a uniform heterogeneous phase is maintained in the reaction mixture by thorough mixing.

* * * * *

UNITED STATES PATENT AND TRADEMARK OFFICE
CERTIFICATE OF CORRECTION

PATENT NO. : 3,965,172
DATED : June 22, 1976
INVENTOR(S) : Zengel et al

It is certified that error appears in the above-identified patent and that said Letters Patent are hereby corrected as shown below:

On front page, in the title, please correct "N,N-Dichloro-..." to read --N,N'-Dichloro...--, both cases. (The correction is a --'-- after the second N)

Signed and Sealed this

First Day of August 1978

[SEAL]

Attest:

RUTH C. MASON
Attesting Officer

DONALD W. BANNER
Commissioner of Patents and Trademarks